United States Patent
Himberg et al.

(10) Patent No.: US 6,555,821 B1
(45) Date of Patent: Apr. 29, 2003

(54) METHOD FOR ANALYSIS OF EXPIRED GAS

(75) Inventors: Jaakko-Juhani Himberg, Helsinki (FI); Olli Laakso, Hyvinkää (FI); Reijo Laaksonen, Lempäälä (FI)

(73) Assignee: Wallac Oy, Turku (FI)

( * ) Notice: Subject to any disclaimer, the term of this patent is extended or adjusted under 35 U.S.C. 154(b) by 0 days.

(21) Appl. No.: 09/544,147

(22) Filed: Apr. 6, 2000

(30) Foreign Application Priority Data

Apr. 8, 1999 (FI) .................................................. 990771

(51) Int. Cl.$^7$ .............................................. G06F 15/20
(52) U.S. Cl. ............................ 250/339.08; 250/339.13; 250/339; 250/343; 364/498
(58) Field of Search ......................... 250/339.08, 255, 250/339.19, 339.07, 343, 339.09, 339.13; 364/498, 502, 497, 499, 500

(56) References Cited

U.S. PATENT DOCUMENTS 5,313,406 A * 5/1994 Kauppinen et al. ......... 364/498
5,741,707 A * 4/1998 Herron et al. ................ 436/25

OTHER PUBLICATIONS

Ahonen et al. "Portable Fourier Transform IR Spectrometer for Use as Gas Analyzer . . . ", Analyst, 121, pp. 1253–1255, 1996.*

Ahonen et al., "Portable Fourier Transform Infrared Spectrometer For Use as a Gas Analyser in Industrial Hygiene," 121 *Analyst* 1253–1255 (1996).

Yang et al., "Application of Multilayer Feed–Forward Neural Networks to Automated Compound Identification in Low–Resolution Open–path FT–IR Spectrometry," 71 *Anal. Chem.* 751–761 (Feb. 1, 1999).

\* cited by examiner

*Primary Examiner*—Bruce Anderson
*Assistant Examiner*—Zia R. Hashmi
(74) *Attorney, Agent, or Firm*—James C. Lydon (57) ABSTRACT

A method for detecting and measuring volatile components in expired gas by sampling the expired gas containing the volatile components; passing infrared radiation from an interferometer through the sample; detecting infrared radiation transmitted from the sample to produce a signal characteristic for the volatile components in the sample; and processing the signal and a set of single component reference library spectra of pure molecular gases in order to detect and calculate the amount of the volatile components in the blood of an individual expiring the gas, including the use of a low resolution FT-IR spectrometer in the detecting and processing.

14 Claims, 5 Drawing Sheets

METHOD FOR ANALYSIS OF EXPIRED GAS

This invention relates to a method for detecting and measuring volatile components of expired gas by the use of low resolution Fourier transformed infrared (FT-IR) spectrometry.

BACKGROUND OF THE INVENTION

Drugs and alcohols account for the majority of acute intoxications treated in hospitals. In many cases drugs and alcohols are ingested together. Symptoms are often non-specific and the intoxication diagnosis is largely based on anamnesis. While anamnesis is often uncertain and confusing, fast and reliable diagnostic methods are needed. Present laboratory methods, however, seldom reveal quickly and accurately the intoxicant and its amount in the body. To detect, and more often to exclude, substances that necessitate immediate special and expensive treatment (e.g. dialysis in the case of methanol intoxication) is important as soon as possible.

Expired human breath contains a number of components that may give valuable information of metabolic processes and substances in blood because only a slender barrier separates air in the alveoli of the lung from the blood in the capillaries. Any volatile compound, such as alcohols, diffuse across the alveolar membrane from the compartment with the higher vapor pressure to the lower—from the blood into the air, or vice versa use (Phillips 1992).

There are few analytical methods with which one can perform real-time identification and quantification of the components of the expired air. Except measuring breath ethanol concentrations of drunken drivers, methods available at present require collecting and concentrating the breath samples before analyzing and are more or less impractical for clinical use (Phillips 1992). At present, instruments that come closest to fulfill the idea of direct identification and of quantification expired breath are based on either infrared (IR) spectroscopy or mass spectrometry (MS).

Since mid 1980's, IR-techniques have been applied for breath ethanol testing. The instruments used have been made more specific for alcohol by using several optical IR-filters or using electrochemical sensors as a second independent detector (Jones et al. 1996). Infrared spectroscopy is one of the fastest methods to analyze gas mixtures. A quantitative infrared analysis of one or few components in a gas mixture is a relative simple task if an isolated absorption peak can be found for each component. Difficulties arise if the characteristic peaks of the compounds overlap, or unknown compounds exist. In these cases laborious methods like gas chromatography have been used. More recently, the problems of spectral overlap have been attacked by applying chemometric methods such as classical least square methods to digitized Fourier transformed IR-spectral (FT-IR) data (Jaakkola et al. 1997).

U.S. Pat. No. 5,313,406 (Kauppinen et al. 1994) describes procedures for analyzing multicomponent FT-IR spectra for unknown mixtures of gases.

OBJECT AND SUMMARY OF THE INVENTION

The object of the present invention is to provide a method for detecting and measuring volatile components in expired gas.

The invention provides a method for detecting and measuring volatile components in expired gas by sampling the expired gas containing said volatile components;

passing infrared radiation from an interferometer through the sample;

detecting infrared radiation transmitted from the sample to produce a signal characteristic for said volatile components in the sample; and processing said signal and a set of single component reference library spectra of pure molecular gases in order to detect and calculate the amount of said volatile components in the blood of an individual expiring said gas, comprising the use of a low resolution FT-IR spectrometer in said detecting and processing.

The invention explicitly provides a method that makes use of low resolution FT-IR in the mid infrared range and reference libraries comprising gases that would or could be included in the composition of expired breath and said method thus also provides a method that is applicable for the detecting and measuring of volatile components in expired gas using apparatus of reasonable cost and suitable for ambulatory use.

DETAILED DESCRIPTION OF THE INVENTION

A preferred embodiment of the method comprises a portable GASMET® analyzer that can be taken to the patient and used to analyze gas expired by the patient. If the patient is conscious he can actively exhale into the sampling device of the equipment, if not, standard techniques (e.g. by intubating) to obtain a sample of expired gas from an unconscious patient can be used. The sampled expired gas is led through a measuring chamber and an IR spectrum in the mid infra-red (MIR) range, wavenumber range 4000 $cm^{-1}$ to 900 $cm^{-1}$, is obtained within a measuring time of 20 s to 1 min. The analyzer compares the sum spectrum obtained to spectrums of known samples within its library. If a good fit is obtained about 95% or more of the spectrum can be explained for. The more complete the library the better the chance to get a good fit. A good library includes several spectrums of the same substance of different concentration in spite Beer's law to ensure optimal fitting in cases where Beer's law does not apply accurately. Samples for the library are saturated with water to be comparable to expired gases that are as well saturated with water. A good fit enables a quantitative, accurate and reliable result.

Low resolution, not more than 4$cm^{-1}$, preferably from 4 $cm^{-1}$ to 16 $cm^{-1}$, and longer measuring time, up to 1 min, generally improves results. When the water vapor content is high, low resolution improves results. It is especially advantageous that there is no need for high resolution making it possible to use a FT-IR analyzer which is light and thus portable. This is a prerequisite for many important applications such as quick ambulatory use for intoxicated patients.

DEFINITIONS AND PREFERRED EMBODIMENTS

Volatile components in expired gas can include organic solvents e.g. methanol, ethanol, isopropanol, acetone, toluene, various components of paints as well as methane, butane, ketones and ammonia. These compounds can appear in the breath when they have been consumed and/or inhaled intentionally or unintentionally, or because of a pathological disorder (e.g. acetone in the breath of patients with diabetes).

Alternatively compounds to be detected and processed can involve substances intentionally administered for varying purposes, e.g. urea can be administered and analyzed for purposes of e.g. testing renal function; anesthetics can be analyzed by the method from inspired and/or expired gases for purposes of monitoring the anesthesia of a patient; and test compounds containing carbon isotope $^{13}C$ can be administered to study how it is metabolized to $^{13}CO_2$, which can be analyzed from the expired gas since it can be differentiated from $^{12}CO_2$ by FT-IR.

The invention will be described in more detail by the following study designed to evaluate the usefulness of a low resolution FT-IR-analyzer with a multicomponent analysis software, originally developed for industrial purposes, in analysis of exhaled gas with special concern on ethanol and methanol.

SUMMARY OF STUDY

The study was designed to evaluate the usefulness of a low resolution FT-IR analyzer with a multicomponent analysis software, originally developed for industrial purposes, in analysis of exhaled air with special concern on ethanol and methanol.

Fast and reliable diagnostic methods are needed for detection or exclusion of industrial solvents as a cause of intoxications. Analyzing human breath reveals the presence of any volatile substance.

A portable FT-IR multicomponent point-of-care analyzer was developed for exhaled breath. The analyzer proved to be accurate and precise in laboratory tests for simultaneous measurement of methanol and ethanol in water. Ethanol, in addition to normal contents of breath, was simultaneously analyzed in human experiments and the results correlated well with blood samples.

FT-IR method has a traceable calibration to physical properties of the analyte. The measured spectra can also be saved and analyzed later. Breath analysis with FT-IR is fast and easy and no preparation of the sample is needed.

EXPERIMENTAL SECTION

Apparatus

The FT-IR spectrometer (Gasmet™, Temet Instruments Oy, Helsinki, Finland) was equipped with multicomponent analysis software (Calcmet™, Temet Instruments Oy, Helsinki, Finland) and modified Genzel interferometer (GICCOR™, Temet Instruments Oy, Helsinki, Finland). The material of the windows and the substrate of the beamsplitter were $BaF_2$. The volume of the continuous flow White-type multi-pass gas cell was 200 ml and the absorption path length 2.0 m. In this study gas cell temperature was set to 50° C. Mirrors of the gas cell were gold coated. The IR radiation source was silicon carbide. Peltier-cooled MCT detector was operated in the wavenumber range from 4000 $cm^{-1}$ to 900 $cm^{-1}$. All the spectra were measured at 8 $cm^{-1}$ resolution and the scan rate was 10 scans/s.

Quantification was performed automatically by using modified classical least squares fitting algorithm (CLS), which uses a maximum amount of pre-computed information to make the analysis simple and fast (Jaakkola et al. 1997). The analysis is based on Beer's law which assumes that the absorbances of the components in the gas phase are directly proportional to their concentrations. The multicomponent analysis algorithm fits the measured unknown spectrum using a set of single component reference library spectra. The baseline of the unknown spectrum is generated mathematically to account for baseline fluctuation. The reliability of the analysis can be characterized from the resulting residual spectrum which should be random noise in the ideal case (Saarinen and Kauppinen 1991).

The FT-IR spectrometer was calibrated with ethanol (AaS, Oy Alko Ab, Helsinki, Finland), methanol (>99.8%, Merck, Darmstadt, Germany), $CO_2$ (>99.9%, AGA, Helsinki, Finland), acetone (>99.8%, Merck, Darmstadt, Germany) and $H_2O$. The reference spectra were made by injecting ethanol, methanol, acetone or water into a heated mixing chamber, where the liquid was vaporized and mixed with flowing nitrogen gas (>99.5%, AGA, Helsinki, Finland). GC-syringes (Hamilton 1700-series™, Hamilton Company, Reno, Nev., USA) and a stepmotor (Cole-Parmer Instrument Company, Vernon Hills, Ill., USA) were used to control the injection rate. The flow rate of nitrogen was measured with Tylan FC260 (Tylan General GMBH, Munich, Germany) mass flow controller. Different reference gas dilutions were generated by adjusting liquid samples injection rate. The maximum error in preparing a reference dilution was calculated to be ±2.5% for alcohols on the basis of flow rate errors and injection rate errors. $CO_2$ reference dilutions were generated by mixing $N_2$ and $CO_2$. The reference spectra were recorded at concentrations ranging from 20 to 2000 ppm for ethanol and methanol, from 2.6% to 8.6% for $CO_2$.

The regions of the spectrum used for the analysis were 910–1300 $cm^{-1}$, 2000–2100 $cm^{-1}$ and 2500–3450 $cm^{-1}$. Alcohols have strong C—O stretching bands between 1000 and 1100 $cm^{-1}$ and strong C—H stretching bands between 2800 and 3000 $cm^{-1}$. The software is able to automatically ignore absorbance peaks over the limit defined by user, in this case 0.8 A.U. However, no such peaks were detected in the analysis region during measurement of clinically relevant concentrations. Spectral regions of 1300–2000 $cm^{-1}$, 2100–2500 $cm^{-1}$ and 3450–4000 $cm^{-1}$ were excluded from analysis because of the strong absorbance of water and $CO_2$ in these regions. In the breath tests $CO_2$ was measured using spectral region of 2000–2100 $cm^{-1}$. Water and acetone were included in the analysis, too.

Design

This study consisted of laboratory measurements and three human experiments:

Laboratory Measurements

Detection limits (DL) were defined by using equation D=X+3d, where X is the average of measured concentrations at zero analyte level (30 measurements) and d is the standard deviation of measurement results of the blank (*Instructions for measurements of gaseous emissions, VDI* 2449).

Vaporous ethanol and methanol mixtures in water were made by bubbling nitrogen gas through a corresponding liquid mixture. The purpose of measuring mixtures of ethanol and methanol was to test the applicability of the instrument for determining more than one alcohol in a gas mixture containing a large amount of water vapor like human exhaled breath. Particularly, the measurements were performed with a large ethanol:methanol ratio in order to investigate whether the instrument is able to determine a low concentration of methanol in the presence of a large amount of ethanol.

The linearity between measured alcohol concentrations in the gas phase and alcohol concentrations in liquid was checked and water-air partition coefficients (lwa) were determined by using equation lwa=cRT/p, where c=liquid concentration (mol/dm3), R=gas constant (0.08206 dm3atm/molK), T=temperature (K) and p=partial pressure in gas phase (atm). All measurements were made at room temperature (21±1.0° C.) and at ambient pressure. The measurement time was 1 minute and each mixture was measured 10 times. The alcohol concentration in the liquid to be bubbled ranged from 0 to 31 w-‰ and corresponded to vaporous concentration range from 0 to 3000 or 4000 ppm (ethanol and methanol respectively).

Human Experiments

Three separate experiments were performed. The first experiment was focused on repeatability of the breath test and the second on determining the accuracy. The third was made to assess the effect of the sample flow resistance on analysis results. Altogether eight healthy volunteer men participated in these trials. Each of them gave their informed consent.

At the beginning of the protocol each of the men ingested a calculated dose of ethanol to achieve a blood ethanol concentration of about 1 g/l. Breath samples were collected and analyzed similarly in all experiments. Immediately after one deep inhalation the whole lung vital capacity was blown via moisture and bacteria filter (Pall BB22-15, Pall Biomedical Products Co, New York, USA) through a 200 ml gas cell. Ethanol and $CO_2$ concentrations were measured at 2 s intervals (1 s scanning time) during the exhalation to determine exhaled ethanol and profiles. The last 200 ml of exhaled air was trapped in the gas cell for exact analysis (2 or 3 measurements, 1 min scanning time each).

To test the repeatability of the breath test in the second experiment, five consecutive measurements were made at five different blood ethanol levels. On-line flow and pressure measurements were also made. A Datex AS/3™ (Datex-Engström, Helsinki, Finland) anesthesia monitor with a side stream spirometry unit was used (Meriläinen et al. 1993). One subject participated in this experiment.

To test the accuracy of the breath test, breath and venous blood samples were taken at three points:

1) blood ethanol concentration (BEC) rising (absorption phase),
2) BEC at its height (plateau phase) and
3) BEC declining (postabsorptive phase).

At each point a blood sample and three breath samples were taken. Blood samples were assayed by a gas chromatographic head-space method. Six subjects participated in this experiment.

During the study the gas cell was further developed. Larger fittings to the gas cell were made in order to decrease the sample flow resistance. The third experiment was performed to measure the effect of the sample flow resistance on the analysis results. Four different resistance levels were caused by blocking the outlet opening so that the resulting mean pressures were from 1.3 kPa (full open) to 4.1 kpa (corresponding the opening in the previous version). Measurements started immediately after ingestion of the ethanol and lasted to the late postabsorption phase. One subject participated in this experiment.

Results

Laboratory Measurements

Correlation between concentrations of ethanol (EC) or methanol (MC) and corresponding largest absorbances at 1049 $cm^{-1}$ for ethanol (EA) or 1057 $cm^{-1}$ for methanol (MA) was calculated from reference spectra. Nine different concentrations for ethanol and eight for methanol were measured. Correlation was practically linear even at high concentrations:

$$EA = 3.53 \times 10^{-4} \times EC - 8.30 \times 10^{-4}, \quad r^2 = 0.9990;$$

$$MA = 4.12 \times 10^{-4} \times MC + 6.37 \times 10^{-3}, \quad r^2 = 0.9993.$$

Results of the bubbling tests are presented in tables 1 to 3. Detection limits were 0.9 ppm and 1.2 ppm for ethanol and 0.9 ppm and 1.3 ppm for methanol in $N_2$ matrix and $N_2$+3.0% water matrix, respectively. Linearity between ethanol (LiqEC) or methanol (LiqMC) concentrations (w-‰) in the bubbled alcohol-water solution and the corresponding vapor (VapEC or VapMC, ppm) was excellent:

$$\text{Vap}EC = 92.43 \times \text{Liq}EC, \quad r^2 = 0.9998;$$

$$\text{Vap}MC = 128.06 \times \text{Liq}MC, \quad r^2 = 1.0000.$$

Adding 3.17 w-‰ ethanol into the methanol-water solution did not affect the methanol analysis:

$$\text{Vap}MC = 126.26 \times \text{Liq}MC, \quad r^2 = 1.0000.$$

Figure 1:
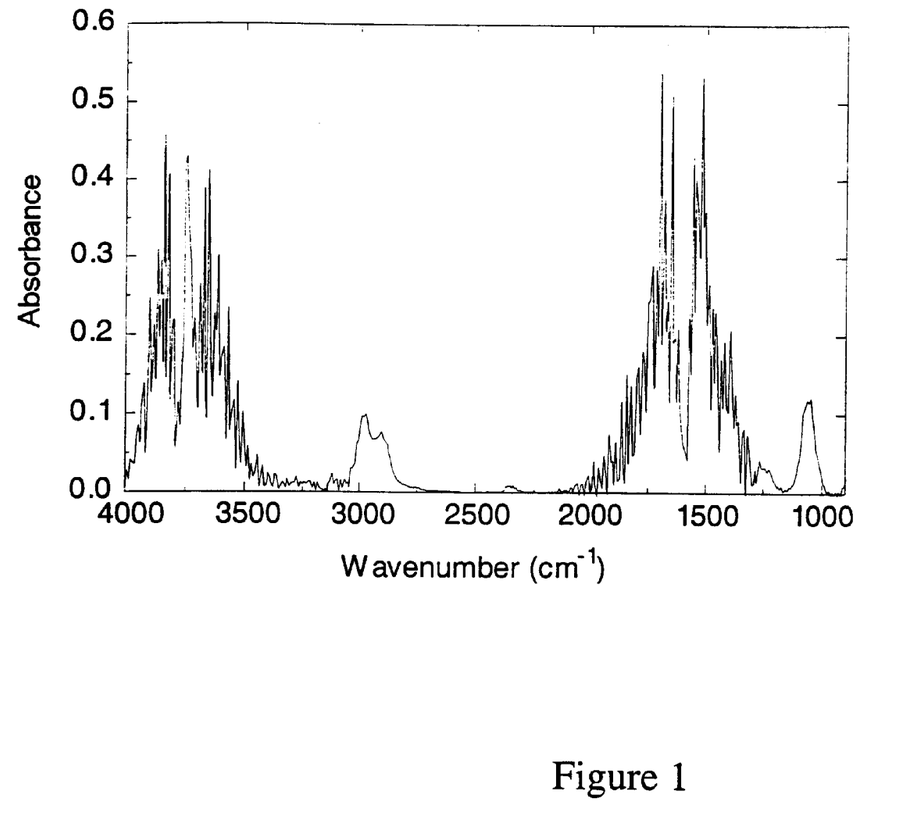
FIG. 1 shows a spectrum of mixture of methanol and ethanol in water.
Figure 2:
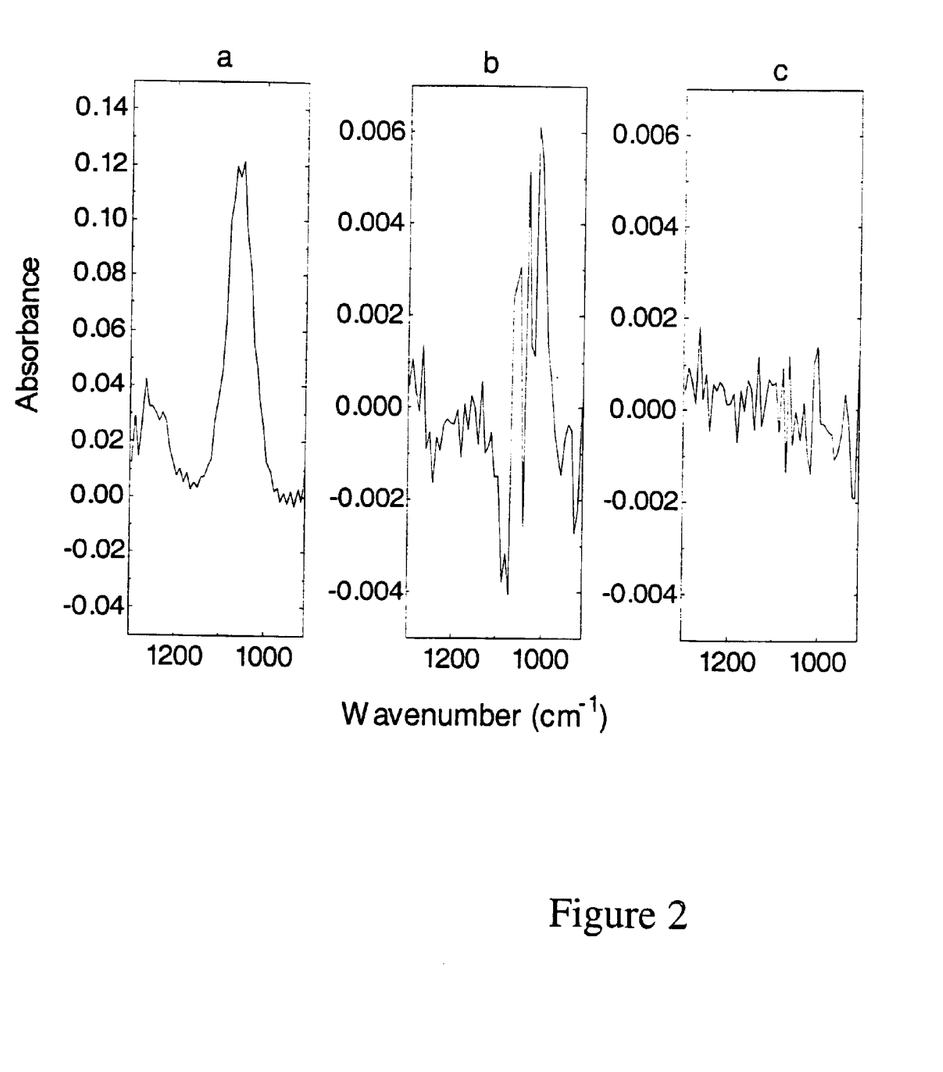
FIG. 2 shows stepwise analysis of a mixture of ethanol and methanol in water.

A typical spectrum measured in bubbling test is presented in FIGS. 1 and 2. FIG. 1 shows a spectrum of a mixture of methanol and ethanol in water at 21±1° C., with 3.17 w-‰ ethanol in liquid phase and 310 ppm in the gas phase and 0.159 w-‰ methanol in liquid phase and 22.4 ppm in the gas phase. Regions of analysis were 910–1300 $cm^{-1}$, 2000–2100 $cm^{-1}$ and 2500–3450 $cm^{-1}$. FIG. 2 shows a stepwise analysis of a mixture of ethanol and methanol in water. The spectra are expanded and absorbance scales changed showing region 910–1300 $cm^{-1}$ from the spectrum in FIG. 1. FIG. 2a shows the spectrum before analysis, 2b an unsatisfactory residual spectrum after analysis (reference spectra included in the analysis: ethanol and water) and 2c the residual spectrum turned to pure noise after methanol was added to analysis components library. Mean [±SD] water-air partition coefficient was calculated to be 5817 [217] for methanol and 5576 [97] for ethanol at 21.0±1.0° C. and at 1 atm pressure.

TABLE 1

Results of bubbling tests: Measured concentrations of methanol in gas phase and corresponding methanol concentration in water.

| Mixture | Concentration of methanol in liquid (w-%) | Concentration of methanol in gas phase (ppm) |
|---|---|---|
| 1 | 0.101 | 13 ± 0.2 |
| 2 | 0.203 | 26.9 ± 0.1 |
| 3 | 0.301 | 41.6 ± 0.3 |
| 4 | 0.501 | 61 ± 1 |
| 5 | 1.59 | 204 ± 2 |
| 6 | 3.17 | 402 ± 2 |
| 7 | 6.34 | 805 ± 4 |
| 8 | 9.51 | 1207 ± 5 |
| 9 | 15.9 | 2031 ± 14 |
| 10 | 31.7 | 4067 ± 28 |

Results are averaged from 10 spectra measured at 21.0 ± 1.0° C., 1 atm. The analysis region was 910–1300 $cm^{-1}$, 2000–2100 $cm^{-1}$ and 2500–3450 $cm^{-1}$. Results are expressed as mean ± standard deviation.

TABLE 2

Results of bubbling tests: Measured concentrations of ethanol in gas phase and corresponding ethanol concentration in water.

| Mixture | Concentration of ethanol in liquid (w-%) | Concentration of ethanol in gas phase (ppm) |
|---|---|---|
| 1 | 0.202 | 19.2 ± 0.1 |
| 2 | 0.5 | 45.7 ± 0.3 |
| 3 | 1 | 94 ± 1 |
| 4 | 1.58 | 148 ± 2 |
| 5 | 3.16 | 305 ± 4 |
| 6 | 6.33 | 587 ± 4 |
| 7 | 9.49 | 907 ± 6 |
| 8 | 15.8 | 1466 ± 11 |
| 9 | 31.6 | 2907 ± 4 |

Results are averaged from 10 spectra measured at 21.0 ± 1.0° C., 1 atm. The analysis region was 910–1300 $cm^{-1}$, 2000–2100 $cm^{-1}$ and 2500–3450 $cm^{-1}$. Results are expressed as mean ± standard deviation.

TABLE 3

Results of bubbling tests: Measured concentrations of methanol and ethanol in gas phase and corresponding methanol concentration in a mixture of water and 3.17 W-% ethanol.

| Mixture | Concentration of methanol in liquid (w-%) | Concentration of methanol in gas phase (ppm) | Concentration of ethanol in gas phase (ppm) |
|---|---|---|---|
| 1 | 0.102 | 14.2 ± 0.4 | 295 ± 2 |
| 2 | 0.159 | 22.2 ± 0.4 | 314 ± 4 |
| 3 | 0.222 | 30.2 ± 0.5 | 298 ± 3 |
| 4 | 0.317 | 43.4 ± 0.4 | 304 ± 2 |
| 5 | 0.95 | 120 ± 2 | 296 ± 4 |
| 6 | 1.59 | 201 ± 3 | 303 ± 5 |
| 7 | 3.18 | 402 ± 2 | 300 ± 2 |
| 8 | 6.36 | 806 ± 7 | 293 ± 3 |
| 9 | 15.9 | 2006 ± 3 | 289 ± 1 |

Results are averaged from 10 spectra measured at 21.0 ± 1.0° C., 1 atm. The analysis region was 910–1300 $cm^{-1}$, 2000–2100 $cm^{-1}$ and 2500–3450 $cm^{-1}$. Results are expressed as mean ± standard deviation.

Human Experiments

Figure 3:
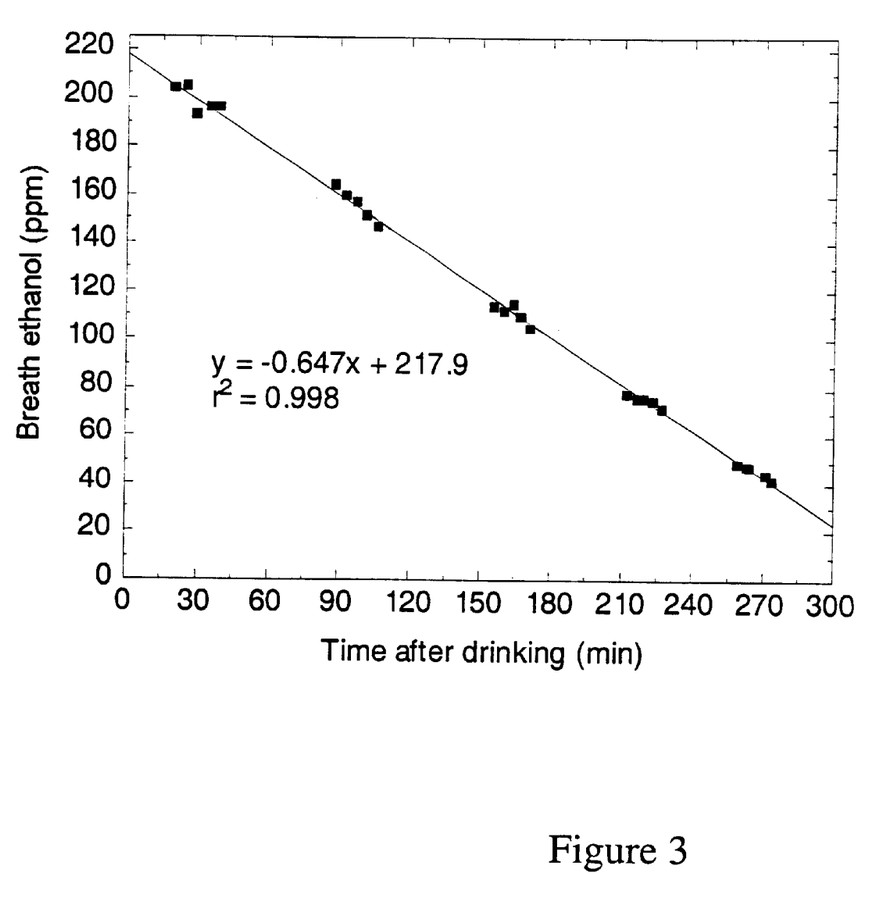
FIG. 3 shows the concentration of ethanol in breath as a function of time after drinking.

Repeatability of the breath test could not be determined because of the continuous ethanol elimination. Each five measurement series took 18–20 min and there was a declining trend of ethanol concentrations within each of the five measurements series demonstrated in FIG. 3 showing the concentration of ethanol in breath as a function of time after drinking (one subject, five series of five consecutive measurements).

Accuracy of the breath test was satisfactory. Within each of the three measuring points of time the ethanol concentrations measured in exhaled breath (BrEC) correlated well with blood concentrations (BEC): at the postabsorptive phase $$BrEC = 203 \times BEC, \quad r^2 = 0.81.$$

Blood:breath ratio ranged from 1616 to 2466 at 34° C. (absorptive to post-absorptive phase, respectively).

Figure 4:
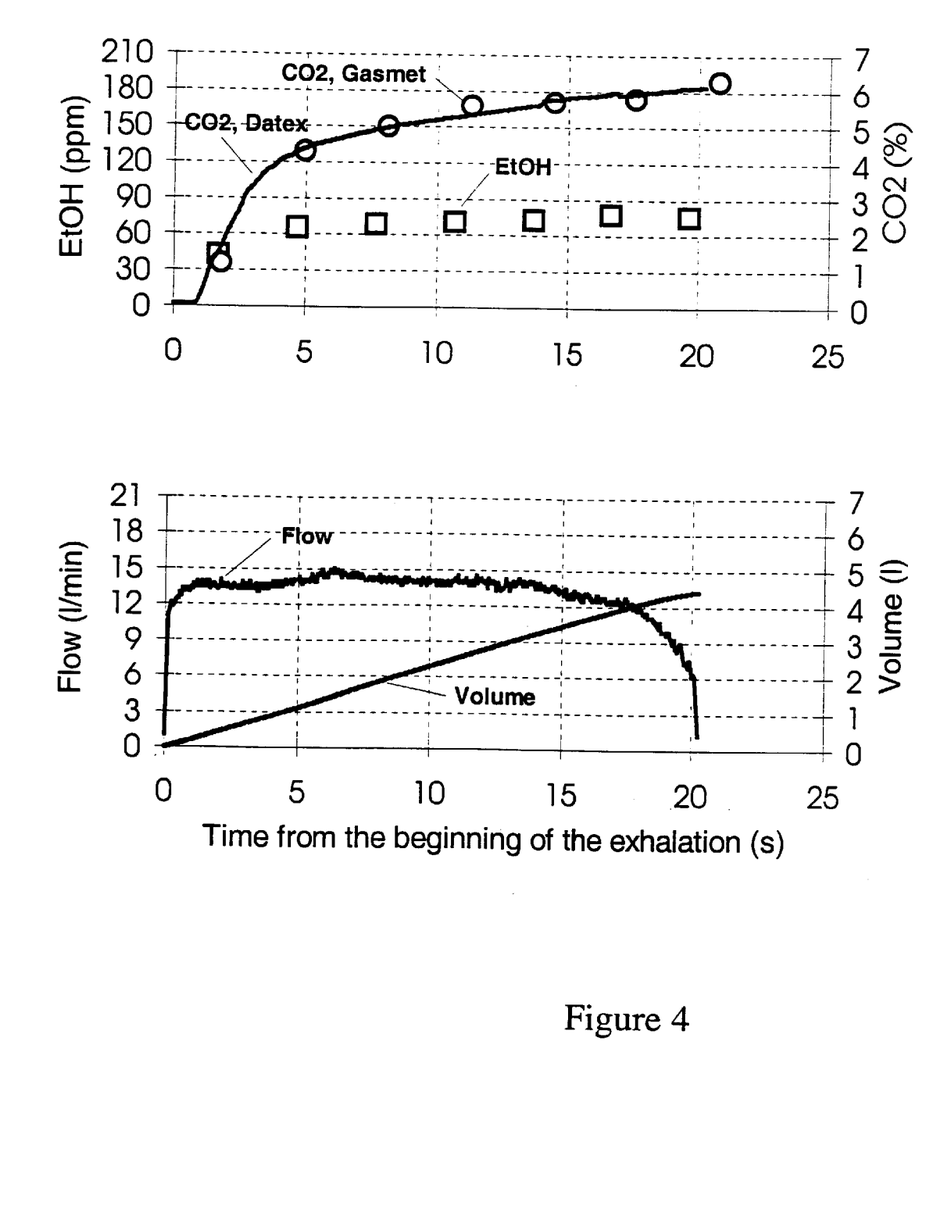
FIG. 4 shows a typical exhalation profile after drinking.

The patient-analyzer interface of the early version was not satisfactory. Blowing into the gas cell caused over 3 kPa pressure (peak pressure over 4 kPa), while the flow remained mostly under 15 l/min. The mean volume exhaled was 4 l and the mean blowing time was 20 s. A typical exhalation profile is shown in FIG. 4 in which the circles and squares show Gasmet™ results (10 scans/analysis; flow, cumulative volume and $CO_2$ measured at 40 ms intervals by Datex-Engström AS/3™).

Figure 5:
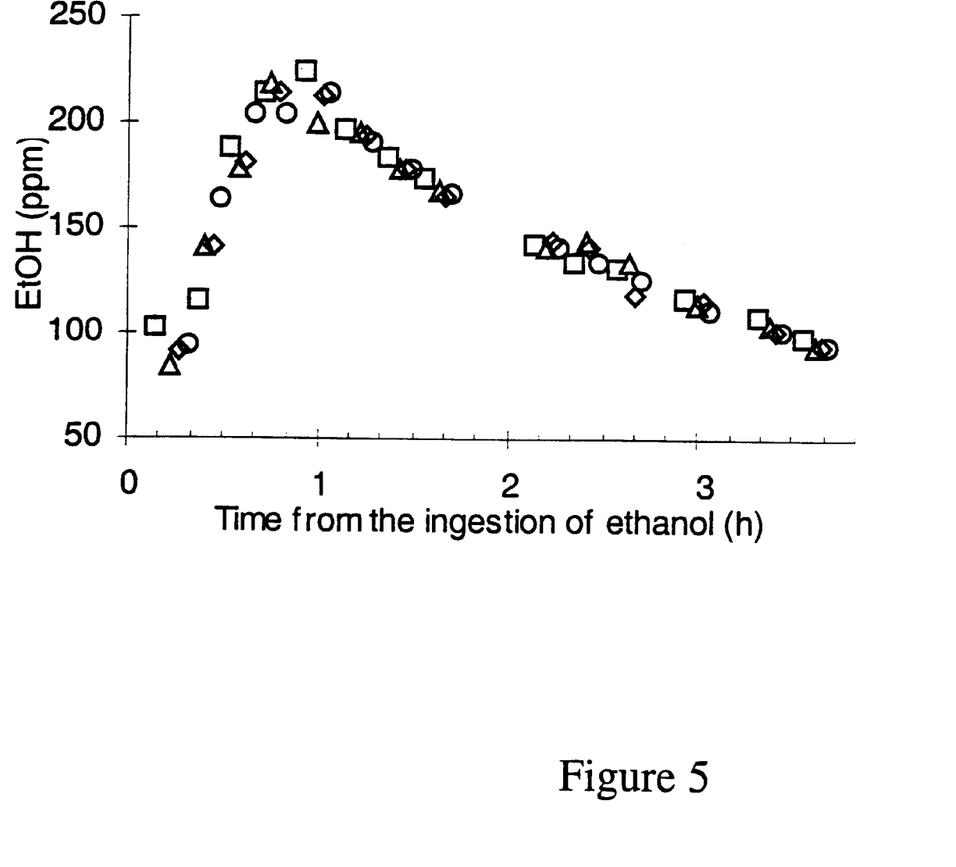
FIG. 5 shows the effect of resistance to blow on measured exhaled ethanol concentration.

Blowing into the gas cell with larger fittings was very much easier than to the previous version. The sample flow exceeded even 100 l/min, and the pressure remained mostly under 1.5 kPa. The measured exhaled ethanol concentration did not change even though the resistance to blow was changed. FIG. 5 shows the effect of resistance to blow on measured exhaled ethanol concentration. In this example ethanol (51 g) was given to a man (80 kg) and four different measuring cell openings were used to alter resistance to blow. Delivery pressures were 1.3 kpa (square), 2.3 kPa (triangle), 3.6 kPa (rhomb) and 4.1 kPa (circle). The concentration of $CO_2$, however, increased from 3.1% to 4.2% as the rising resistance induced longer blowing time (3.4 s and 8.3 s, respectively).

DISCUSSION

The low resolution FT-IR-spectrometry proved precise and accurate for measurement of ethanol in human breath. Laboratory measurements support the assumption that methanol and also methanol-ethanol combinations can be reliably analyzed in the concentration region 0.1–31.0 w-‰. Blowing into the gas cell with large cell fittings was convenient.

Quantitative analysis with low resolution. High degree of spectral overlap and the nonlinearity of the absorbances as a function of concentration are the strongest objections to the use of low resolution spectra for gas phase analysis. Low resolution has, however, many advantages over high resolution. The most obvious advantages are simpler design of the instrument and shorter measurement time or higher signal-to-noise ratio (Jaakkola et al. 1997).

For a quantitative analysis the most important property of the spectrum is the signal to noise ratio (SNR). The error limits of the analysis results using modified classical least squares fitting algorithm (CLS) are directly proportional to the baseline noise in the spectrum and to the square root of the spectral resolution. Thus the SNR of the spectrum has stronger effect on the uncertainty of the quantitative analysis results than the instrumental resolution. Resolution and SNR depend on each other: increasing the resolution also increases the noise if the instrumental conditions are the same. To optimize the results it is necessary to maximize SNR by lowering the resolution (Jaakkola et al. 1997).

The non-linear behavior of absorbance as a function of concentration, if not corrected, can produce significant quantitative errors because CLS algorithm assumes a linear relationship between absorbance and concentration. The extent of the non-linearity will vary depending on the natural line width of the absorption band and the resolution of the spectrometer. The correction can be accomplished by determining the non-linearity factor from the reference spectra at different concentrations (Bak and Larsen 1995). The effect of non-linearity can also be minimized by measuring a sufficient amount of reference spectra within the non-linear concentration range.

Non-linearity can be an advantage in increasing the dynamic range of quantitative analysis: It is possible to measure high concentrations with low resolution instrument, because at low resolution the measured absorbances are lower than at high resolution. This is a significant advantage in the case of a low concentration component required to be measured in the presence of strongly absorbing components with high degree of spectral overlap (Saarinen and Kauppinen 1991).

Additionally, in the case of low resolution, the measured lineshape of a molecule is determined by instrumental function of the spectrometer so that pressure broadening effects are reduced (Saarinen and Kauppinen 1991).

Detection Limits, Linearity and Repeatability

The sensitivity of the device investigated exceeds the clinical needs. In the case of serious ethanol and/or methanol intoxication the breath alcohol concentration ranges widely (from dozens to several thousand ppm), being however over ten times higher than the detection limits of alcohols (1.2 ppm for ethanol and 1.3 ppm for methanol in 3.0% water matrix with 1 minute measurement time). Likewise, the accuracy according to the laboratory measurements is excellent. Clinical repeatability test showed some deviation of the consecutive measurements, which was mostly due to lowering of the subject's blood ethanol concentration during the measuring series. The single measurements could not be performed more frequently, because two one minute analyses were to be made and the purging of the gas cell takes its time, too.

For ideal dilute solutions Henry's law predicts a linear relationship between the partial vapor-pressure of the solute and its concentration in the aqueous phase. The vapor pressure of the solute depends strongly on temperature and slightly on pressure. The literature values for Henry's law constants in the terms of water-air partition coefficients were calculated to be at 25° C. and at 1 atm 5260 or 5334 for methanol and 3890 or 4918 for ethanol (Hine and Mookerjee 1975, Davidovits et al. 1995). These results agree with mean water-air partition coefficients calculated from our results (5817 for methanol and 5576 for ethanol at 21.0±1.0° C. and at 1 atm).

Up to 20 different reference spectra can be loaded at the same time and as many different substances can be detected and measured simultaneously (Hakuli et al. 1995). Even unknown or unexpected substances are to be noticed. One of our subjects had an exceptional amount of methane in his breath and this was detected by the automatic analysis protocol as unsatisfactory residual spectrum. Closer investigation revealed a typical methane configuration in the residual spectrum. When methane reference was added to the library, the residual spectrum turned to pure noise.

Blood-breath Equilibrium

For medicolegal purposes, a blood:breath ratio of 2100:1 is used to convert the result of breath ethanol analysis into the corresponding blood alcohol concentration. Instead of being determined in vivo at the alveolar-capillary membrane, the blood:breath alcohol ratio has been derived from simultaneous measurements of blood alcohol and breath alcohol concentrations (Jones 1978). We measured (at 34° C.) blood:breath ratio of 1616 [276], 2216 [304] and 2466 [216] (mean [SD]) at 15 [8–12], 54 [47–67] and 155 [93–211] (median [range]) minutes after ingestion of the ethanol bolus. The results agree with previous investigations by showing higher and more constant values in the postabsorptive phase. The absolute value in the postabsorptive phase agrees with the literature value of 1200–2500 (Baselt 1989). The blood:breath ratio of one subject remained remarkably low even in the postabsorptive phase. That could be explained by delayed absorption of ethanol (Simpson 1989). If the measurements of this subject had been ignored the measured breath ethanol concentrations (BrEC) would have correlated excellently with the blood ethanol (BEC) concentrations (BrEC=199×BEC, r2=0.95), in the postabsorptive phase.

To get a good estimate of blood alcohol concentration the end expiratorial or alveolar sample has been evaluated necessary and sufficient, on the other hand. Alveolar samples were collected in this experiment, too. Breath alcohol profiles generated during exhalation have been discussed lately and even some mathematical models (Lubkin et al. 1996, Gullberg 1990 and 1992). have been derived in order to get better blood-breath alcohol correlations. It has been investigated, that besides alveolar membrane the mucosa on the respiratory tract participates significantly in changing highly water soluble substances like alcohols (Hlastala et al. 1988 and George et al.). This makes understanding of exhalation profiles of alcohols more difficult than that of carbon dioxide, which is equilibrated merely in alveoli (Lubkin et al. 1996). Carbon dioxide reaching its plateau is, though, a good marker of satisfactory sample, because the theories described above conclude that alcohols reach their high exhaled concentrations before carbon dioxide.

Factors affecting breath alcohol profile and the concentration reached are: breathing pattern prior to breath test (hypo- or hyperventilation), breath temperature and delivery pressure. The latest deserves attention, because higher pressures than 2.5 kPa have been shown to prevent attaining an exhalation plateau and getting systematically too low alcohol concentrations in the exhalation (Gullberg 1990) and could explain the marginally high blood:breath ratio measured in this study. In this experiment the sample flow resistance of the early gas cell version was high and delivery pressures were even over 3.0 kPa (FIG. 4). The resistance of the new gas cell with wide openings remained low with the mean delivery pressure of 1.3 kPa. No alteration of breath ethanol concentration was nevertheless noticed in the experiment made with different gas cell outlet openings.

The moisture and bacterial filter used seemed to adsorb some ethanol, too. That did not affect the measurements at the end expiratory level—even though the filters were used for many times. The filters seemed to saturate with water and ethanol very soon.

Other Major Solvents

Theoretically, and based on pilot tests, it seems obvious that in addition to ethanol and methanol any solvent or denaturant (e.g. isopropanol, methylethylketone) could be detected in the exhaled breath. Ethylene glycol is an unfortunate exception. It has a high boiling point and vaporizes so little that it can not be detected in the exhaled breath by the equipment described.

CONCLUSIONS

The low resolution FT-IR spectrometry proved precise and accurate for measurement of ethanol in human breath. Laboratory measurements support the assumption that methanol and also methanol-ethanol combinations can be reliably analyzed. The measured spectra are saved and can be analyzed later on. This is invaluable, not only for identifying unknown compounds, but also for medicolegal purposes. Contrary to other portable alcohol and solvent detectors, FT-IR spectrometry is a direct measuring method, not based on any chemical reactions. Analysis with low resolution FT-IR has several advantages over analysis with conventional methods: it is easy to use, fast and portable. No expensive chemicals or other single use material (except the filter) are needed.

REFERENCES

Bak, J.; Larsen, A. Applied Spectroscopy 1995, 49, 437–443.

Baselt, R. C.; Year Book Medical Publishers: Chicago, USA, 1989.

Davidovits, P.; Hu, J. H.; Worsnop, D. R.; Zahniser, M. S.; Kolb, C. E. Faraday Discuss 1995, 100, 65–82.

George, S. C.; Babb, A. L.; Hlastala, M. P. Journal of Applied Physiology 1993, 75, 2439–2449.

Gullberg, R. G. Journal of Analytical Toxicology 1990, 14, 358–367.

Gullberg, R. G. Journal of Forensic Sciences 1992, 37, 1363–1372.

Hakuli, A.; Kytökivi, A.; Lakomaa, E.-L.; Krause, O. Analytical Chemistry 1995, 67, 1881–1886.

Hine, J.; Mookerjee, P. K. Journal of Organic Chemistry 1975, 40, 292–298.

Hlastala, M. P.; Ralph, D. D.; Babb, A. L. Advances in Experimental Medicine and Biology 1988, 227, 33–38.

Instructions for measurements of gaseous emissions, VDI 2449; Verein Deutcher Ingenieure, VDI.

Jaakkola, P.; Tate, J. D.; Paakkunainen, M.; Kauppinen, J.; Saarinen, P. Applied Spectroscopy 1997, 51, 1159–1169.

Jones, A. W. Journal of Studies on Alcoholism 1978, 39, 1931–1939.

Jones, A. W.; Andersson, L.; Berglund, K. J Anal Toxicol 1996, 20, 522–7.

Kauppinen, J.; Saarinen, P. U.S. Pat. No. 5,313,406, 1994.

Lubkin, S. R.; Gullberg, R. G.; Logan, B. K.; Maini, P. K.; Murray, J. D. Alcohol and Alcoholism 1996, 31, 61–67.

Meriläinen, P.; Hänninen, H.; Tuomaala, L. Journal of Clinical Monitoring 1993, 9, 374–380.

Phillips, M. Scientific American 1992, 267, 52–57.

Saarinen, P.; Kauppinen, J. Applied Spectroscopy 1991, 45, 953–963.

Simpson, G. J Anal Toxicol 1989, 13, 120–3.

What is claimed is:

1. A method for detecting and measuring volatile components in expired gas comprising sampling the expired gas containing said volatile components;

passing infrared radiation from an interferometer through the sample;

detecting infrared radiation transmitted from the sample to produce a signal characteristic for said volatile components in the sample; and processing said signal and a set of single component reference library spectra of pure molecular gases in order to detect and calculate the amount of said volatile components in the blood of an individual expiring said gas, comprising the use of a low resolution FT-IR spectrometer in said detecting and processing.

2. The method of claim 1, wherein the detection is carried out at a resolution of not more than 4 cm$^{-1}$.

3. The method of claim 1, wherein the detection is carried out within the mid infrared wavenumber range from 4000 cm$^{-1}$ to 900 cm$^{-1}$.

4. The method of claim 1, in which the detection is carried out at intervals ranging from 20 seconds to 1 minute.

5. The method of claim 1, in which the single component reference library spectra being processed comprise spectra of at least two pure molecular gases selected from the group of methanol, ethanol, isopropanol, toluene, $NH_3$, $^{13}CO_2$, methane, acetone and volatile keto compounds at different concentrations in admixture with water vapor.

6. The method of claim 5, wherein the pure molecular gases selected for calibration are methanol and ethanol.

7. The method of claim 6, wherein the reference spectra of methanol and ethanol are recorded at a concentration ranging from 20 to 2000 ppm.

8. The method of claim 1, wherein the detection is carried out on a heated sample.

9. The method of claim 8, in which the sample is heated to a temperature ranging from 400° C. to 600° C.

10. The method of claim 1, in which the sample is filtered before passing infrared radiation therethrough.

11. The method of claim 1, wherein said low resolution FT-IR spectrometer has been adapted to sample gas expired from an individual at a sample flow of at least 15 l/minute and a pressure of less than 1.5 kPa.

12. The method of claim 11, wherein said low resolution FT-IR spectrometer includes a continuous flow gas cell having a volume of about 200 ml.

13. The method of claim 11, wherein said low resolution FT-IR spectrometer has an absorption path length of about 2.0 m.

14. The method of claim 2, wherein said detection is carried out at a resolution of from 4 cm$^{-1}$ to 16 cm$^{-1}$.

* * * * *